(12) United States Patent
Nishihara et al.

(10) Patent No.: US 9,339,170 B2
(45) Date of Patent: May 17, 2016

(54) MEDICAL DEVICE INCLUDING SELF-PROPELLED CAPSULE ENDOSCOPE

(75) Inventors: Hironori Nishihara, Shiga (JP); Naotake Ohtsuka, Shiga (JP); Yasunori Shindo, Shiga (JP); Kazuhide Higuchi, Osaka (JP)

(73) Assignee: MU LTD., Shiga (JP)

( * ) Notice: Subject to any disclaimer, the term of this patent is extended or adjusted under 35 U.S.C. 154(b) by 87 days.

(21) Appl. No.: 14/237,183

(22) PCT Filed: Sep. 3, 2012

(86) PCT No.: PCT/JP2012/072335
§ 371 (c)(1),
(2), (4) Date: Feb. 5, 2014

(87) PCT Pub. No.: WO2013/035665
PCT Pub. Date: Mar. 14, 2013

(65) Prior Publication Data
US 2014/0187862 A1    Jul. 3, 2014

(30) Foreign Application Priority Data

Sep. 5, 2011 (JP) ................................. 2011-193255
Feb. 15, 2012 (JP) ................................. 2012-030455

(51) Int. Cl.
*A61B 1/00* (2006.01)
*A61B 1/01* (2006.01)
*A61B 1/04* (2006.01)

(52) U.S. Cl.
CPC ......... *A61B 1/00156* (2013.01); *A61B 1/00158* (2013.01); *A61B 1/041* (2013.01); *A61B 2034/732* (2016.02)

(58) Field of Classification Search
CPC ........... A61B 1/00156; A61B 1/00158; A61B 1/041; A61B 2019/2253; A61B 2019/2257; A61B 2019/2261
See application file for complete search history.

(56) References Cited

U.S. PATENT DOCUMENTS 3,358,676 A * 12/1967 Frei .................... A61B 1/00158
273/456
6,014,580 A *  1/2000 Blume .................. A61B 19/52
128/899

(Continued)

FOREIGN PATENT DOCUMENTS

JP    2001-179700 A    7/2001
JP    2006-62071 A    3/2006

(Continued)

OTHER PUBLICATIONS

Official Communication issued in International Patent Application No. PCT/JP2012/072335, mailed on Oct. 2, 2012.

(Continued)

*Primary Examiner* — John P Leubecker
(74) *Attorney, Agent, or Firm* — Keating & Bennett, LLP

(57) ABSTRACT

A medical device includes a capsule endoscope in which a magnet having a magnetization direction in an axial direction is mounted and a fin portion is provided at a rear end of an endoscope main body, and which can be self-propelled through the inside of a body; and a capsule controller which controls self-propulsion of the capsule endoscope from the outside of the body by generating a static magnetic field whose direction is controlled three-dimensionally, and an alternating magnetic field orthogonal to the static magnetic field. The capsule endoscope rotates upon receiving the static magnetic field so that the magnetization direction of the magnet is parallel to the direction of the static magnetic field and the fin portion vibrates by bending with movement of the magnet in response to the alternating magnetic field.

11 Claims, 12 Drawing Sheets

(56) References Cited

U.S. PATENT DOCUMENTS

| | | | | |
|---|---|---|---|---|
| 6,015,414 | A * | 1/2000 | Werp | A61B 19/20 606/108 |
| 6,128,174 | A * | 10/2000 | Ritter | A61B 19/22 361/141 |
| 7,727,169 | B1 * | 6/2010 | Lewkowicz | A61B 1/00156 600/109 |
| 8,500,509 | B2 * | 8/2013 | Orozco | A63H 23/14 40/409 |
| 8,500,619 | B2 * | 8/2013 | Brown | A61B 17/22012 128/899 |
| 2002/0055734 | A1 * | 5/2002 | Houzego | A61B 25/01 604/891.1 |
| 2007/0244388 | A1 * | 10/2007 | Sato | A61B 1/00147 600/424 |
| 2010/0049033 | A1 * | 2/2010 | Kawano | A61B 1/00158 600/424 |
| 2010/0234685 | A1 * | 9/2010 | Juloski | A61B 1/00158 600/117 |
| 2010/0298635 | A1 * | 11/2010 | Hata | A61B 1/00158 600/104 |

FOREIGN PATENT DOCUMENTS

| | | |
|---|---|---|
| JP | 2008-43125 A | 2/2008 |
| JP | 2008-279019 A | 11/2008 |
| WO | 2008/144559 A2 | 11/2008 |

OTHER PUBLICATIONS

Official Communication issued in corresponding European Patent Application No. 12830813.7, mailed on Feb. 19, 2015.

* cited by examiner

MEDICAL DEVICE INCLUDING SELF-PROPELLED CAPSULE ENDOSCOPE

TECHNICAL FIELD

The present invention relates to a medical device including a capsule endoscope capable of being self-propelled through the inside of a body and a capsule controller that controls self-propulsion of the capsule endoscope from the outside of the body.

BACKGROUND ART

In recent years, a medical device that examines the inside of a body using a capsule endoscope capable of being self-propelled through the inside of the body is known. The capsule endoscope in this medical device generally imposes less burden on a subject because, unlike conventional endoscopes, it does not require a tube that passes through the gullet or the like for operating the endoscope. When a subject swallows the capsule endoscope, the capsule endoscope moves through the inside of the body according to a peristaltic movement of the stomach or the intestines while capturing images of the surroundings with an internal camera, and the captured images are transmitted to a capsule controller that controls the self-propulsion of the capsule endoscope from the outside of the body and are stored in a storage medium. Thereafter, the capsule endoscope is discharged outside from the anus.

Such a self-propelled capsule endoscope can move to a destination to be examined by itself as well as moving passively according to the peristaltic movement. For example, Patent Document 1 discloses a capsule endoscope in which a magnet having a magnetization direction in a direction orthogonal to an axial direction (longitudinal direction) is mounted and a propulsive power generating portion having a spiral structure is provided at the rear end in the axial direction. This capsule endoscope is configured such that the magnet rotates in response to a rotational magnetic field generated by a capsule controller disposed at the outside of the body, and the propulsive power generating portion rotates with rotation of the magnet, whereby propulsive power in the axial direction is generated.

Patent Document 2 discloses a capsule endoscope in which a magnet having a magnetization direction in an axial direction (longitudinal direction) is mounted and a fin portion is provided at the rear end in the axial direction. This capsule endoscope is configured such that the magnet vibrates in response to an alternating magnetic field generated by a capsule controller disposed at the outside, and the fin portion vibrates by bending with the vibration of the magnet to push surrounding liquid backward, whereby propulsive power in the axial direction is generated. In Patent Document 2, the position of an electromagnet that generates a one-directional alternating magnetic field is controlled by a guide rail and a lift so that the capsule endoscope is moved to a destination to be examined.

Since the attitude of the capsule endoscope of Patent Document 2 is stable so that the fin portion bends in the direction of the alternating magnetic field, the capsule endoscope can obtain stable images and perform examinations easily as compared to the capsule endoscope of Patent Document 1 in which images captured by the internal camera are likely to rotate or be inclined unstably with rotation of the propulsive power generating portion. Moreover, since the capsule endoscope of Patent Document 2 can move a large amount of liquid backward with strong force by means of the fin portion, it is possible to easily increase the propulsive power with a small size as compared to the capsule endoscope of Patent Document 1 in which the propulsive power is obtained by rotation of the propulsive power generating portion, and to reduce the possibility that the body walls (wall surfaces inside the body) are damaged with friction.

PRIOR ART DOCUMENTS

Patent Documents

Patent Document 1: Japanese Patent Application Publication No. 2001-179700
Patent Document 2: Japanese Patent Application Publication No. 2008-279019

SUMMARY OF THE INVENTION

Problem to be Solved by the Invention

Such a capsule endoscope that is propelled by vibration of the fin portion as disclosed in Patent Document 2 has several advantages. In the meantime, since the path along which the capsule endoscope advances through the inside of the body comes in various types including a relatively wide area like the stomach and a crooked areas like the intestines, it is important to control the moving direction of the capsule endoscope. The capsule endoscope propelled by vibration of the fin portion can change the moving direction thereof by applying a bias magnetic field in parallel to the alternating magnetic field.

However, in the method of applying the bias magnetic field in parallel to the alternating magnetic field, it is not always easy to accurately move the capsule endoscope to a destination to be examined since the capsule endoscope gradually changes the moving direction thereof while moving.

The present invention has been made in view of the foregoing, and an object thereof is to provide a medical device including a self-propelled capsule endoscope that is propelled through the inside of a body by vibration of a fin portion and a capsule controller that controls self-propulsion of the capsule endoscope from the outside of the body, the medical device being capable of precisely controlling the moving direction of the capsule endoscope easily.

Means for Solving the Problem

In order to attain the object, according to a preferred embodiment of the present invention, there is provided a medical device including: a capsule endoscope in which a magnet having a magnetization direction in an axial direction is mounted and a fin portion is provided at a rear end in the axial direction of an endoscope main body, and which can be self-propelled through the inside of a body; and a capsule controller that controls self-propulsion of the capsule endoscope from the outside of the body by generating a static magnetic field whose direction is controlled three-dimensionally and an alternating magnetic field orthogonal to the static magnetic field, wherein the capsule endoscope is configured such that the capsule endoscope rotates upon receiving the static magnetic field so that the magnetization direction of the magnet is parallel to the direction of the static magnetic field and the fin portion vibrates by bending with movement of the magnet in response to the alternating magnetic field, whereby propulsive power in the axial direction is generated.

Preferably, the capsule controller generates the static magnetic field and the alternating magnetic field by means of a magnetic field generating portion that includes three sets of Helmholtz coils. Alternatively, the capsule controller generates the static magnetic field and the alternating magnetic field by means of a magnetic field generating portion that includes three sets of coil pairs, and coils that constitute each of the three sets of coil pairs each have a circumferential shape that is selected from a polygonal shape, an elliptical shape, and a circular shape. In this case, it is preferable that coils that constitute any one or two sets of the three sets of coil pairs or the three sets of coil pairs each have a circumferential shape that is an oblong polygonal shape or an elliptical shape. Alternatively, the capsule controller generates the static magnetic field and the alternating magnetic field by means of a magnetic field generating portion that includes one set of Helmholtz coils and two sets of electromagnets.

More preferably, the capsule controller is configured to be able to change an amplitude and/or a frequency of the alternating magnetic field and/or to change a magnitude of the static magnetic field. In this case, it is preferable that the amplitude and/or the frequency of the alternating magnetic field and/or the magnitude of the static magnetic field corresponds to a turn angle of a terminal, a tilt angle of a joystick, a moving distance of a lever, or a depression amount of an accelerator.

Further preferably, the direction of the static magnetic field is controlled by an operating unit that uses a handle whose rotational position can be held, and corresponds to a direction of a reference point of the handle. In this case, an inclination angle of the static magnetic field in relation to a horizontal surface is controlled by changing an inclination angle of a shaft of the handle or by changing a moving distance of a movable portion of a slider or a lever. Alternatively, the direction of the static magnetic field is controlled by an operating unit that uses a joystick, and a reference point of a joystick platform is rotated by an angle corresponding to a tilt direction of the joystick, thus the direction of the static magnetic field corresponds to the direction of the reference point. In this case, an inclination angle of the static magnetic field in relation to a horizontal surface is controlled by changing a tilt angle of the joystick platform or by changing a moving distance of a movable portion of a slider or a lever.

Effects of the Invention

According to the medical device of the present invention, since the moving direction of the capsule endoscope in the inside of the body is controlled according to the static magnetic field, and independently from this, the propulsive power is controlled by the alternating magnetic field orthogonal to the static magnetic field, the moving direction and the moving speed of the capsule endoscope can be easily controlled precisely.

BRIEF DESCRIPTION OF DRAWINGS

FIGS. 2A and 2B are external views illustrating a schematic configuration of a capsule endoscope of the medical device, in which FIG. 2A is a side view and FIG. 2B is a plan view;

DESCRIPTION OF EMBODIMENTS

Figure 1:
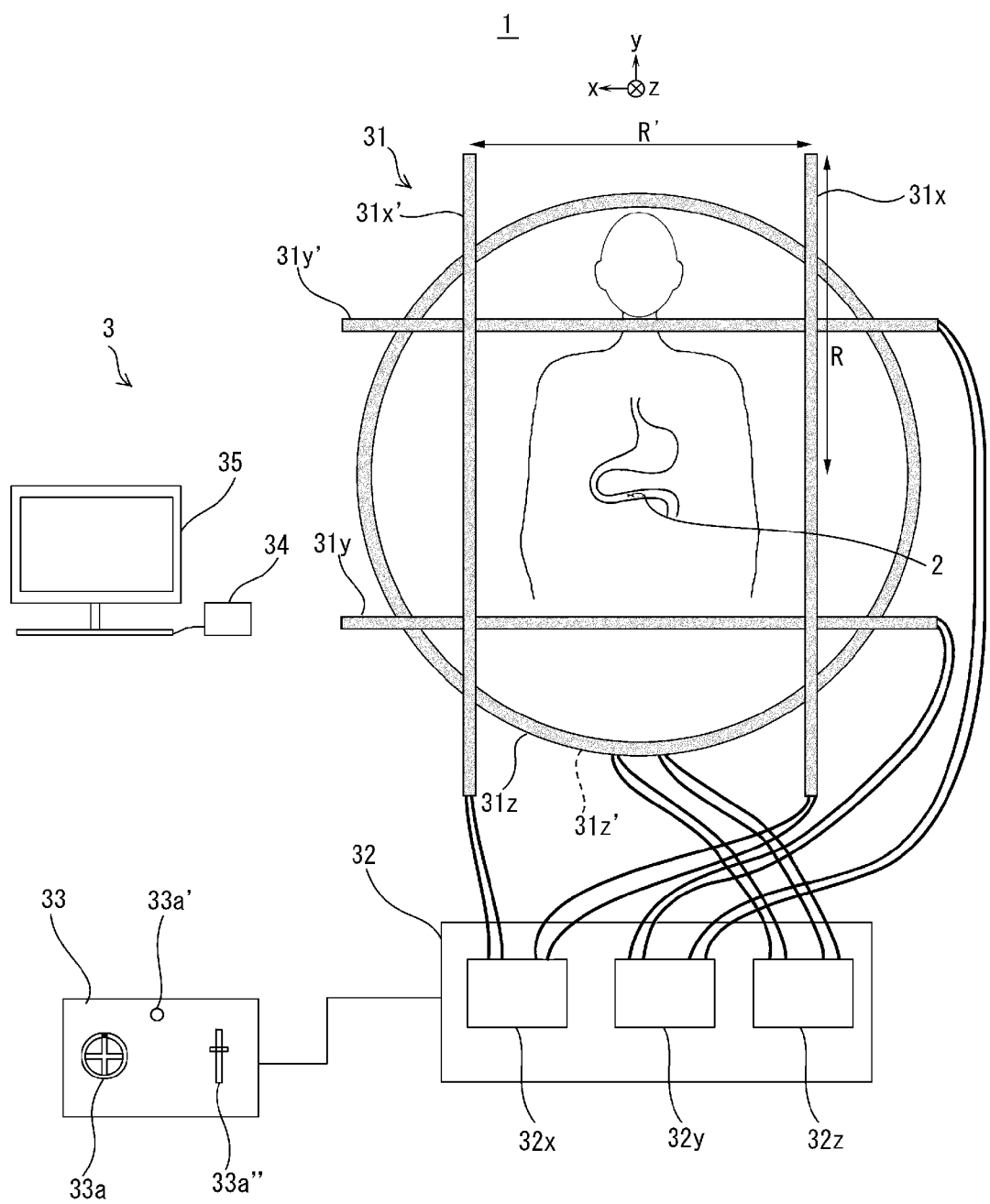
FIG. 1 is a schematic diagram illustrating a configuration of a medical device according to an embodiment of the present invention.

Hereinafter, preferred embodiments of the present invention will be described with reference to the drawings. A medical device 1 according to an embodiment of the present invention performs internal examinations or the like of a subject, and as illustrated in FIG. 1, includes a capsule endoscope 2 that can be self-propelled at the inside of the body of the subject and a capsule controller 3 that controls self-propulsion of the capsule endoscope 2 from the outside of the body. The subject is positioned so that a body portion thereof is located inside a predetermined range defined by a magnetic field generating portion 31 described later of the capsule controller 3 and is examined after swallowing the capsule endoscope 2 from the mouth. The capsule endoscope 2 may be inserted from the anus.

Figure 2A:
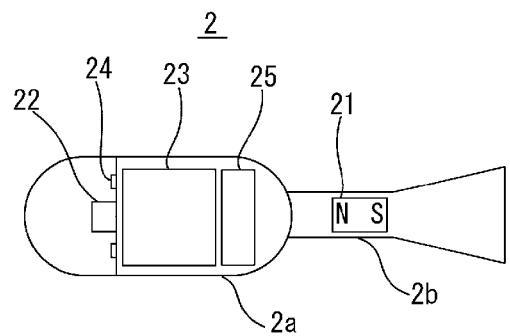
Figure 2B:
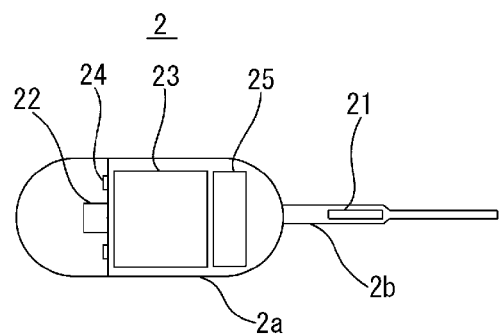

The capsule endoscope 2 is generally an approximately cylindrical endoscope that moves in an axial direction (longitudinal direction), and as illustrated in FIGS. 2A and 2B, includes an endoscope main body 2a in which a camera 22 or the like is mounted and a fin portion 2b in which a magnet 21 having a magnetization direction in the axial direction is mounted. The fin portion 2b is provided at the rear end in the axial direction of the endoscope main body 2a, and specifically, a front end of the fin portion 2b is fixed to the rear end of the endoscope main body 2a directly or with a cap-shaped member or the like interposed. In the present embodiment, the capsule endoscope 2 has such a size that a length in the axial direction is approximately 4.5 cm, for example, and a diameter is approximately 1 cm.

The structure of the endoscope main body 2a is not the point of the present invention, and an existing one that is used in the conventional capsule endoscope can be used. As illustrated in FIGS. 2A and 2B, such an endoscope main body 2a generally includes, in addition to the above-described camera 22, a power supply unit 23 that supplies electric power to respective units of the capsule endoscope 2, an illumination unit 24 that illuminates the outside in order to allow the camera 22 to capture images, a wireless communication unit 25 that wirelessly transmits the images captured by the camera 22 to the capsule controller 3, and the like. A front part (the left part in FIGS. 2A and 2B) of the endoscope main body 2a is transparent so that light can pass through the front part. The camera 22 is constituted of a CCD or the like, the power supply unit 23 is constituted of a battery or the like, and the illuminating unit 24 is constituted of an LED or the like. The wireless communication unit 25 may be configured to wirelessly receive a control signal from the capsule controller 3 to control the camera 22, the illuminating unit 24, and the like.

The magnet 21 of the fin portion 2b is a rod-shaped magnet, and as described above, has the same magnetization direction as the axial direction of the capsule endoscope 2. The magnet 21 is mounted in an elastic member such as a silicon resin. The magnet 21 receives a static magnetic field and an alternating magnetic field orthogonal to the static magnetic field, generated by a magnetic field generating portion 31 described later of the capsule controller 3. Upon receiving the static magnetic field, the magnet 21 rotates so that it is parallel to the direction of the static magnetic field. The capsule endoscope 2 rotates with the rotation of the magnet 21. Moreover, the magnet 21 vibrates in response to the alternating magnetic field. Accordingly, as illustrated in FIG. 3, the fin portion 2b vibrates by bending to push surrounding liquid backward whereby propulsive power in the axial direction is generated.

Figure 3:
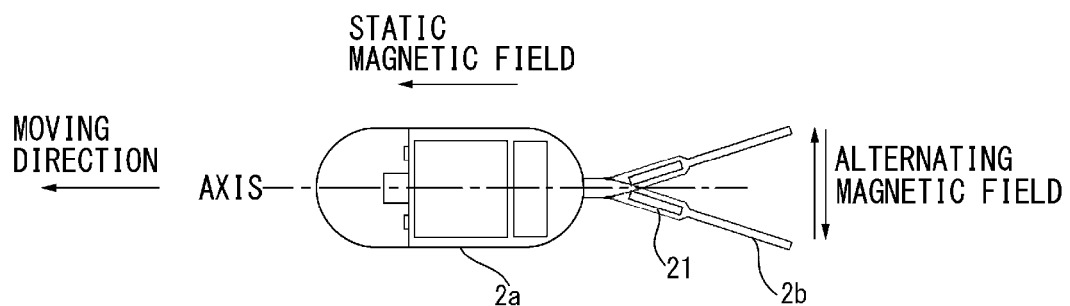
FIG. 3 is a plan view schematically illustrating an example of propulsion of the capsule endoscope of the medical device.

Since the front end of the fin portion 2b is fixed to the endoscope main body 2a and the rear end is open, when the magnet 21 vibrates, the rear end (the S-pole side in FIGS. 2A and 2B) of the magnet 21 moves greatly according to the alternating magnetic field and the front end (the N-pole side in FIGS. 2A and 2B) vibrates with a very small amplitude (see FIG. 3).

The fin portion 2b has a wide side surface such that it bends like the fin of a fish to efficiently push liquid backward. The shape of the side surface is appropriately selected. For example, a posterior part of the side surface may have a trapezoidal shape as illustrated in FIG. 2A, or the fin portion 2b may have a generally round shape or an oblong shape. Moreover, the thickness (a width of a surface orthogonal to the wide side surface) of the fin portion 2b may be set such that the anterior part thereof is thin and the posterior part thereof is thinner as illustrated in FIG. 2B. Or, the entire fin portion 2b may have the same thickness. When an alternating magnetic field is orthogonally incident on the wide side surface of the fin portion 2b so that the fin portion 2b bends, an attitude of the capsule endoscope 2 is stabilized.

Figure 4:
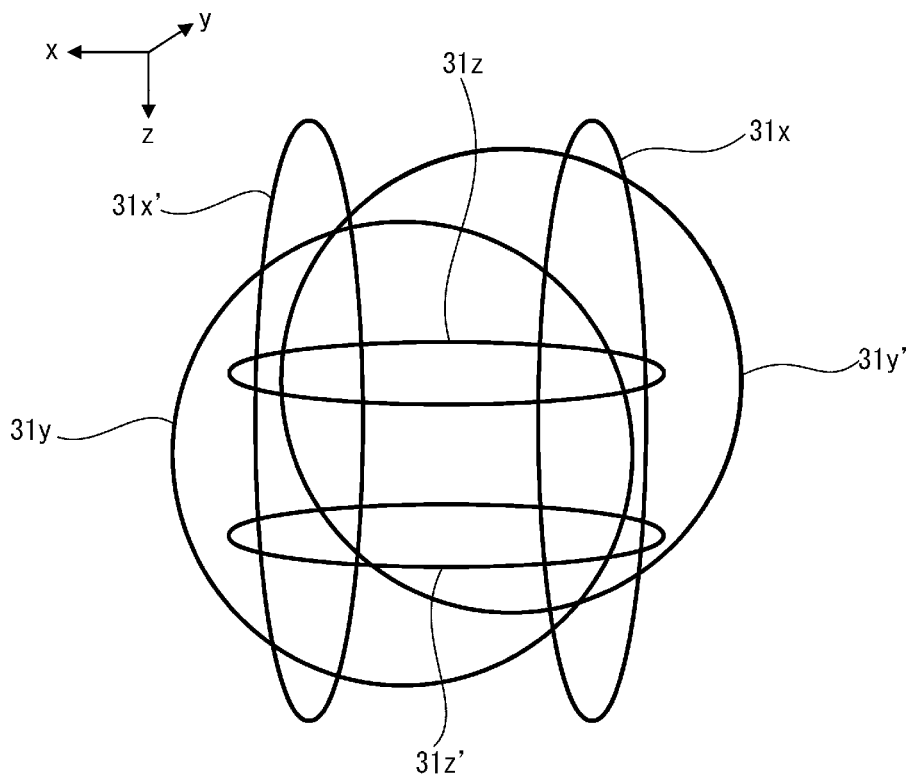
FIG. 4 is a schematic pictorial diagram illustrating a configuration of a magnetic field generating portion of the medical device.

Next, the capsule controller 3 will be described. As illustrated in FIGS. 1 and 4, the capsule controller 3 includes the magnetic field generating portion 31 that surrounds the capsule endoscope 2 from three orthogonal directions. The magnetic field generating portion 31 consists of three sets of Helmholtz coils composed of one set of x-axis Helmholtz coils $31x$ and $31x'$ for generating a magnetic field in an x-axis direction (left-right direction in FIG. 1), one set of y-axis Helmholtz coils $31y$ and $31y'$ for generating a magnetic field in a y-axis direction (up-down direction in FIG. 1), and one set of z-axis Helmholtz coils $31z$ and $31z'$ for generating a magnetic field in a z-axis direction (direction vertical to the drawing sheet in FIG. 1). In FIG. 1, the subject lies or stands up in parallel to the y-axis direction. Moreover, in FIG. 1, one z-axis Helmholtz coil $31z'$ is located behind the other z-axis Helmholtz coil $31z$.

The magnetic field generating portion 31 is configured to generate a static magnetic field that does not change over time and generate an alternating magnetic field that changes over time with a predetermined frequency and amplitude according to a control current from the magnetic field control unit 32 and to generate a combination of a static magnetic field and an alternating magnetic field. The static magnetic field and the alternating magnetic field can be directed in any 3-dimensional direction. Specifically, based on a control signal from the operating unit 33 described later, an x-axis magnetic field control unit $32x$ of the magnetic field control unit 32 supplies such a current that generates an x-axis directional magnetic field component to the x-axis Helmholtz coils $31x$ and $31x'$, a y-axis magnetic field control unit $32y$ supplies such a current that generates a y-axis directional magnetic field component to the y-axis Helmholtz coils $31y$ and $31y'$, and a z-axis magnetic field control unit $32z$ supplies such a current that generates a z-axis directional magnetic field component to the z-axis Helmholtz coils $31z$ and $31z'$.

The x-axis Helmholtz coils $31x$ and $31x'$ have such a structure that cylindrical coils around which a plurality of wires is wound are provided concentrically and in parallel so as to be separated by the same distance R' as a radius R of the coil so that a uniform magnetic field is generated at a central axis. The x-axis Helmholtz coils $31x$ and $31x'$ are configured to be able to generate a uniform magnetic field in the x-axis direction at the central axis by supplying the same directional current to the x-axis Helmholtz coils $31x$ and $31x'$. Such an iron core as used in an electromagnet is not used for generating a magnetic field. In practice, although a small variation generally occurs due to the width, the thickness, and the installing conditions or the like of the coils around which a plurality of wires is wound, it is possible to generate a substantially uniform magnetic field in the x-axis direction in a space near the central axis. For example, an allowable variation of the average distance R' in relation to the average radius R of the coil may be controlled to be within 10% or 20%. The fact that a substantially uniform magnetic field is generated in a space near the central axis is different from that of an electromagnet in which the magnetic field changes greatly depending on the position in the central axis direction. The same is true for the y-axis Helmholtz coils $31y$ and $31y'$ and the z-axis Helmholtz coils $31z$ and $31z'$. Thus, in a certain range near the center of the magnetic field generating portion 31, the combined magnetic field is substantially uniform in any direction, and basically, the capsule endoscope 2 is controlled by the capsule controller 3 in or near this range. In general, it is necessary to arrange the x-axis Helmholtz coils $31x$ and $31x'$, the y-axis Helmholtz coils $31y$ and $31y'$, and the z-axis Helmholtz coils $31z$ and $31z'$ sequentially on the outer side while increasing the radii and gaps (distances) thereof. Moreover, the radii and gaps thereof are not particularly limited, and the order of the radii and gaps thereof is not limited.

The static magnetic field is used for controlling a moving direction of the capsule endoscope 2. The magnetic field control unit 32 supplies a direct current to the three sets of Helmholtz coils of the magnetic field generating portion 31 to generate a static magnetic field so that the direction of the combined static magnetic field corresponds to a target moving direction. By doing so, the magnet 21 of the capsule endoscope 2 rotates quickly so as to be aligned in parallel to the direction of the static magnetic field, and the capsule endoscope 2 rotates with the rotation so as to be aligned in a direction identical to the target moving direction.

Moreover, the alternating magnetic field is used for propelling the capsule endoscope 2. The magnetic field control unit 32 supplies an alternating current to the three sets of Helmholtz coils of the magnetic field generating portion 31 to generate alternating magnetic field components and controls the alternating magnetic field components so that the direction of the combined alternating magnetic field is orthogonal to the static magnetic field. By doing so, the magnet 21 of the capsule endoscope 2 vibrates in a direction approximately orthogonal to the target moving direction, the fin portion 2b vibrates in a direction approximately orthogonal to the target moving direction with the vibration, and as a result, the capsule endoscope 2 is self-propelled in the target moving direction.

Here, in a region near the center of the magnetic field generating portion 31, since the static magnetic field acting on the capsule endoscope 2 is substantially uniform, the capsule endoscope 2 just rotates so that the axis of the capsule endoscope 2 is parallel to the direction of the static magnetic field and is rarely attracted in a specific direction. Thus, it is easy to control the moving direction. Moreover, in a region near the center of the magnetic field generating portion 31, since the dependence on position of the magnitude of the alternating magnetic field acting on the capsule endoscope 2 is very small, it is easy to control the moving speed.

Figure 5:
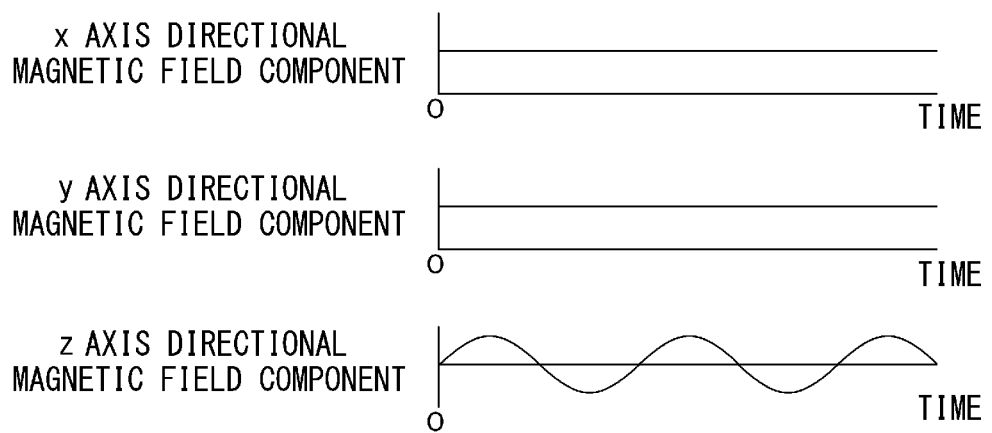
FIG. 5 is a waveform diagram illustrating examples of a magnetic field generated by the magnetic field generating portion of the medical device.
Figure 6A:
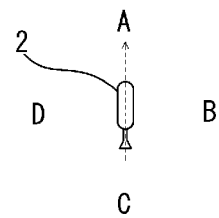
FIGS. 6A to 6D are schematic diagrams illustrating examples of the relationship between the state of a handle of an operating unit of the medical device and the state of the capsule endoscope.
Figure 6A:
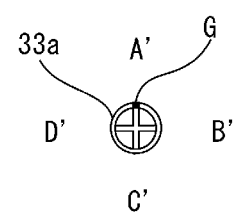
Figure 6B:
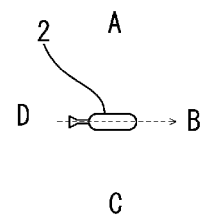
Figure 6B:
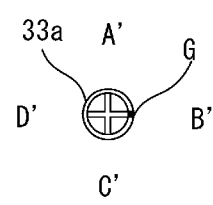
Figure 6C:
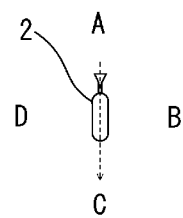
Figure 6C:
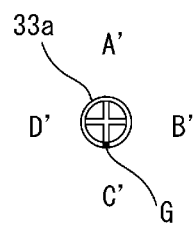
Figure 6D:
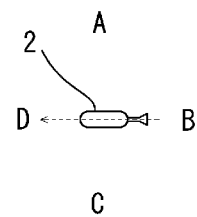
Figure 6D:
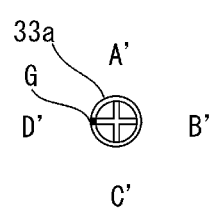

Although the point in time when the static magnetic field and the alternating magnetic field are generated is not particularly limited, since the moving direction is generally quickly determined by the static magnetic field, the static magnetic field may be generated slightly earlier than or simultaneously with the alternating magnetic field. After the static magnetic field is generated, the static magnetic field and the alternating magnetic field may be generated simultaneously and combined. For example, if the moving direction is 45°, 45°, and 90° with respect to the x, y, and z axes, respectively, the x- and y-axis directional magnetic field components may be static magnetic field components of the same values and the z-axis directional magnetic field may be an alternating magnetic field as illustrated in FIG. 5.

By changing the amplitude and the frequency of the alternating magnetic field, the moving speed can be decreased according to the control signal from the operating unit 33 described later so that the details of the images from the capsule endoscope 2 can be observed, or the propulsive power can be increased according to the control signal so that the capsule endoscope 2 can easily pass through an area where it is difficult for the capsule endoscope 2 to pass. Moreover, by changing the magnitude of the static magnetic field, the magnitude of force directed to the target moving direction can be controlled according to the control signal from the operating unit 33 described later so that the capsule endoscope 2 can be easily directed in an area where it is usually difficult for the capsule endoscope 2 to be directed to the target moving direction due to an obstacle or the like. In order to change the amplitude and the frequency of the alternating magnetic field, the amplitude and frequency may be adjusted so as to correspond to the turn angle of a terminal 33a' (see FIG. 1) described later or the tilt angle of a joystick 33b described later. Or, a manually operated lever (not illustrated) or a foot accelerator (not illustrated) may be prepared so that the amplitude and frequency may be adjusted so as to correspond to a moving distance of the lever or a depression amount of the accelerator. Further, in order to change the magnitude of the static magnetic field, the magnitude of the static magnetic field may be changed whenever the amplitude and the frequency of the alternating magnetic field are changed, or may be changed independently by the terminal 33a', the lever, or the like.

Moreover, when the alternating magnetic field starts to be generated, it possibly occurs that the angle between the vibrating direction of the fin portion 2b and the direction of the alternating magnetic field is close to orthogonal so that it is difficult for the fin portion 2b to vibrate. In this case, the direction of the alternating magnetic field may be changed within a range where the direction is orthogonal to the static magnetic field according to the control signal from the operating unit 33.

In this manner, since the moving direction and the propulsive power (moving speed) of the capsule endoscope 2 can be controlled independently, it is easy to accurately move the capsule endoscope 2 to a destination to be examined.

Moreover, the capsule controller 3 includes the operating unit 33 that is operated by an examiner as described above. The operating unit 33 controls the moving direction or the like of the capsule endoscope 2 using an operating device such as the handle 33a as illustrated in FIGS. 1 and 6A to 6D or the joystick 33b as illustrated in FIGS. 8A to 8D. The direction of the static magnetic field is controlled based on a signal output by the operating unit 33. In addition to this, a device that controls the amplitude, frequency, or direction of the alternating magnetic field, a device that controls the magnitude of the static magnetic field, and the like may be provided. Moreover, in the present embodiment, a communicating unit 34 receives in-vivo images transmitted from the capsule endoscope 2 and the images are displayed on a display device 35. The examiner can operate the operating device such as the handle 33a or the joystick 33b while observing the images.

The operating unit 33 that uses the handle 33a may be configured as follows. The handle 33a is configured so that a rotational position thereof is held. For example, when a reference point G of the handle 33a is at the upper side (the position A'), the static magnetic field is directed to the direction A (see FIG. 6A). The static magnetic field can rotate sequentially from the direction A to the directions B, C, and D by 90° each. When the static magnetic field is directed to the direction A, the capsule endoscope 2 is directed to the direction A. An image from the capsule endoscope 2 is an image of the direction A. When the examiner observes the image from the capsule endoscope 2 and wants the capsule endoscope 2 to go straight on, the examiner adjusts the moving speed using the terminal 33a' (see FIG. 1) or the like without turning the handle 33a.

When the examiner observes the image and wants to change the moving direction of the capsule endoscope 2, the examiner turns the handle 33a leftward or rightward. For example, when the examiner observes the image and wants to change the moving direction of the capsule endoscope 2 rightward by 90°, the examiner turns the handle 33a by 90° rightward. By doing so, the reference point G of the handle 33a is positioned at the right side (the position B'), and the static magnetic field is directed to the direction B (see FIG. 6B), and the capsule endoscope 2 is directed to the direction B. Similarly, in a state where the capsule endoscope 2 is directed to the position B, when the examiner observes the image and wants to change the moving direction of the capsule endoscope 2 rightward by 90°, the examiner turns the handle 33a by 90° rightward. By doing so, the reference point G of the handle 33a is positioned at the lower side (the position C'), and the static magnetic field is directed to the direction C (see FIG. 6C), and the capsule endoscope 2 is directed to the direction C. Similarly, in a state where the capsule endoscope 2 is directed to the position C, when the examiner observes the image and wants to change the moving direction of the capsule endoscope 2 rightward by 90°, the examiner turns the handle 33a by 90° rightward. By doing so, the reference point G of the handle 33a is positioned at the left side (the position D'), and the static magnetic field is directed to the direction D (see FIG. 6D), and the capsule endoscope 2 is directed to the direction D.

Figure 7A:
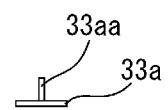
FIGS. 7A to 7C are schematic diagrams illustrating examples of inclination of the handle of the operating unit of the medical device.
Figure 7B:
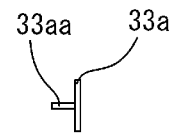
Figure 7C:
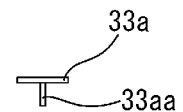
Figure 8A:
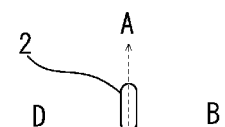
FIGS. 8A to 8D are schematic diagrams illustrating examples of the relationship between the state of a joystick of another operating unit of the medical device and the state of the capsule endoscope.
Figure 8A:
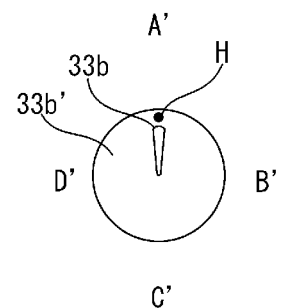
Figure 8B:
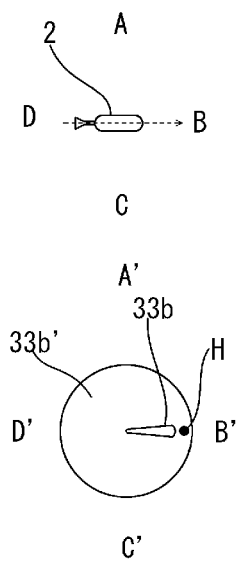
Figure 8C:
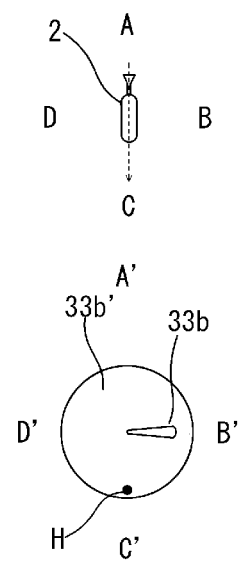
Figure 8D:
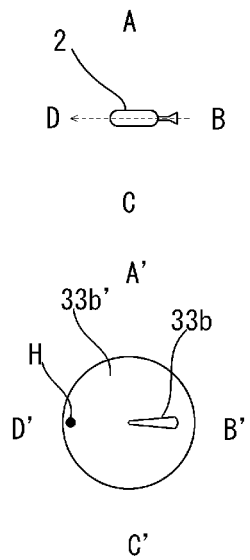

In this manner, the operating unit 33 that uses the handle 33a controls the static magnetic field so as to be directed in the direction corresponding to the reference point G, whereby the moving direction toward the left and right sides of the screen being observed can be controlled by the operation (rotating operation) of the handle 33a. The moving direction toward the upper and lower sides of the screen observed may be controlled by changing the moving distance of a movable portion of a slider 33a" as illustrated in FIG. 1 or changing an inclination angle of a shaft 33aa of the handle 33a as illustrated in FIGS. 7A to 7C so that the static magnetic field can be controlled to be at an optional angle within a range of −90° and 90° with respect to a horizontal surface. For example, the states of the shaft 33aa of the handle 33a, as shown in FIGS. 7A, 7B, and 7C, can be controlled so as to correspond to a case where the static magnetic field is inclined at −90°, 0°, and 90° with respect to the horizontal surface, respectively. In place of the terminal 33a' or the slider 33a", another device form may be naturally further used. For example, a lever may be used instead of the slider 33a". Moreover, the reference point G may be invisible.

The operating unit 33 that uses the joystick 33b may be configured as follows. The joystick 33b rotates the direction of the static magnetic field corresponding to a position of a reference point H of a joystick platform 33b'. The reference point H is automatically (or manually if necessary) rotated by an angle between upper side (the position A') and a tilt direction of the joystick 33b. For example, when the reference point H of the joystick platform 33b' is at the upper side (the position A'), the static magnetic field is directed to the direction A (see FIG. 8A). The static magnetic field can rotate sequentially from the direction A to the directions B, C, and D by 90° each. When the static magnetic field is directed to the direction A, the capsule endoscope 2 is directed to the direction A. An image from the capsule endoscope 2 is an image of the direction A. When the examiner observes the image from the capsule endoscope 2 and wants the capsule endoscope 2 to go straight on, the examiner tilts the joystick 33b toward the upper side (the position A'). By doing so, the capsule endoscope 2 goes straight on at a moving speed corresponding to the tilt inclination angle of the joystick 33b.

When the examiner observes the image and wants to change the moving direction of the capsule endoscope 2, the examiner tilts the joystick 33b in a desired direction. For example, when the examiner observes the image and wants to change the moving direction of the capsule endoscope 2 rightward by 90°, the examiner tilts the joystick 33b rightward. By doing so, the joystick platform 33b' rotates so that the reference point H is at the right side (the position B'), the static magnetic field is directed to the direction B (see FIG. 8B), and the capsule endoscope 2 is directed to the direction B. Similarly, in a state where the capsule endoscope 2 is directed to the direction B, when the examiner observes the image and wants to change the moving direction of the capsule endoscope 2 rightward by 90°, the examiner moves back the joystick 33b so as to stand up and then tilts the joystick 33b rightward again. By doing so, the joystick platform 33b' rotates so that the reference point H is at the lower side (the position C'), the static magnetic field is directed to the direction C (see FIG. 8C), and the capsule endoscope 2 is directed to the direction C. Similarly, in a state where the capsule endoscope 2 is directed to the direction C, when the examiner observes the image and wants to change the moving direction of the capsule endoscope 2 rightward by 90°, the examiner moves back the joystick 33b so as to stand up and then tilts the joystick 33b rightward again. By doing so, the joystick platform 33b' rotates so that the reference point H is at the left side (the position D'), the static magnetic field is directed to the direction D (see FIG. 8D), and the capsule endoscope 2 is directed to the direction D.

Figure 9A:
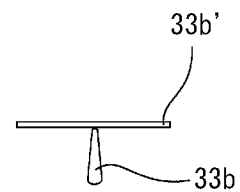
FIGS. 9A to 9C are schematic diagrams illustrating examples of inclination of a joystick platform of the operating unit of the medical device.
Figure 9B:
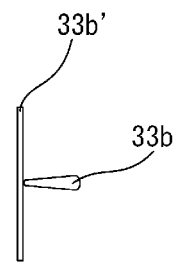
Figure 9C:
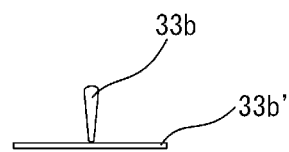

In this manner, the operating unit 33 that uses the joystick 33b controls the static magnetic field so as to be directed in the direction corresponding to the reference point H, whereby the moving direction toward the left and right sides of the screen being observed can be controlled by the operation of the joystick 33b. The moving direction toward the upper and lower sides of the screen observed may be controlled by using the slider 33a' or the like described above or by changing the tilt angle of the joystick platform 33b' as illustrated in FIGS. 9A to 9C so that the static magnetic field can be controlled to be at an optional angle within a range of −90° and 90° with respect to a horizontal surface. For example, the state of the joystick platform 33b' in FIGS. 9A, 9B, and 9C corresponds to a case where the static magnetic field is inclined at −90°, 0°, and 90° with respect to the horizontal surface, respectively. Note that FIGS. 9A to 9C illustrate a state where the joystick 33b stands up. Moreover, in place of the slider 33a", another device form (for example, a lever or the like) may be naturally further used. Moreover, the reference point H may be invisible.

An embodiment in which the capsule controller 3 is configured using the magnetic field generating portion 31 has been described. Since the use of the magnetic field generating portion 31 having three sets of Helmholtz coils enables a magnetic field to become substantially uniform as described above, it becomes easy to control the moving direction and the propulsive power (moving speed). Each set of Helmholtz coils is one set of coil pairs made up of two coils provided concentrically and in parallel. When miniaturization or the like is prioritized, the shape of the coil of any one or two sets of coil pairs or the three sets of coil pairs of the magnetic field generating portion 31 having three sets of Helmholtz coils may be changed, the size of the coil may be changed, and the distance between two coils that constitute the coil pair may be changed. In this case, a magnetic field is not even (not uniform) but changes depending on a location as will be described later.

Figure 10A:
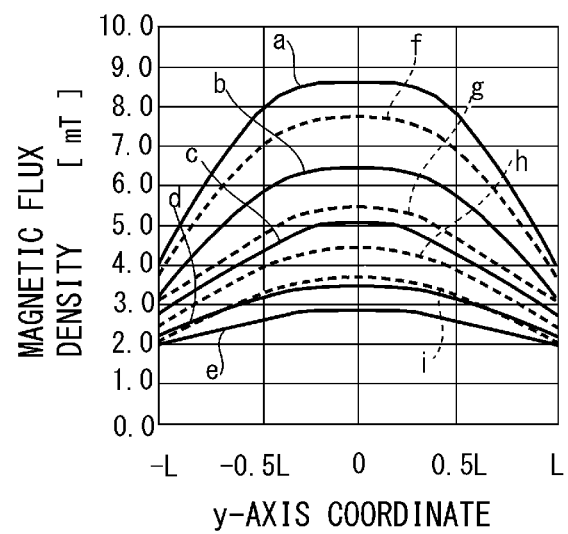
FIGS. 10A to 10C are diagrams illustrating the characteristics of one set of coil pairs obtained for use in a modification of the magnetic field generating portion of the medical device.
Figure 10B:
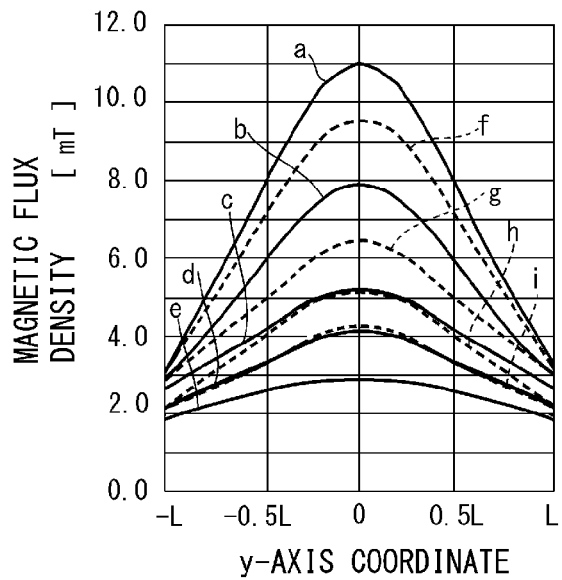
Figure 10C:
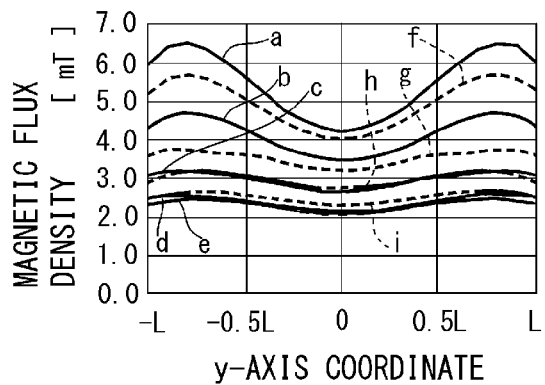
Figure 11A:
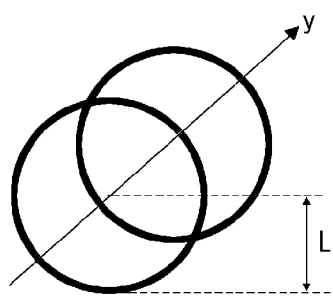
FIGS. 11A to 11C are schematic pictorial diagrams illustrating one set of coil pairs used when obtaining the characteristics of FIGS. 10A to 10C.
Figure 11B:
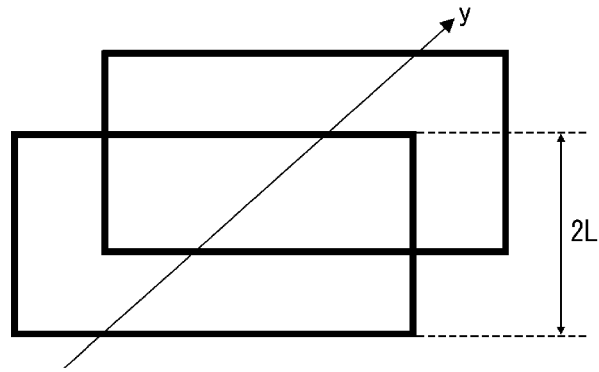
Figure 11C:
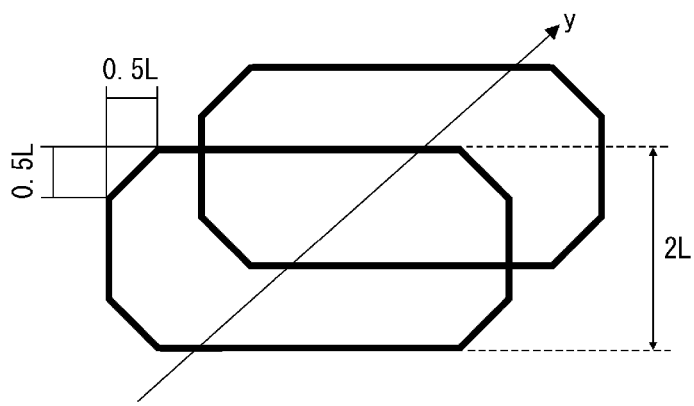

The characteristics illustrated in FIGS. 10A to 10C are obtained by simulating the magnetic flux density in the y-axis direction of a magnetic field when one set of coil pairs is disposed so as to generate a magnetic field in the y-axis direction. The horizontal axis represents a y-axis coordinate value in which the center represents the middle of two coils, and a unit length is L. FIGS. 10A, 10B, and 10C illustrate one set of coil pairs so that the distance between two coils is L, 0.5 L, and 2 L, respectively. A curve "a" in the respective drawings illustrates the characteristics a cylindrical coil the circumferential shape of which is a circle having a radius of L (see FIG. 11A). Curves "b," "c," "d," and "e" in the drawings illustrate the characteristics of a coil the circumferential shape of which is a square having each side of 2 L, a rectangle having a short side of 2 L and a long side of 3 L, a rectangle having a short side of 2 L and a long side of 4 L, and a rectangle having a short side of 2 L and a long side of 5 L, respectively (see FIG. 11B). Curves "f," "g," "h," and "i" in the drawings illustrate the characteristics of a coil the circumferential shape of which is an octagon manufactured by cutting all corners of a quadrangle by a length of 0.5 L (see FIG. 11C). The octagons corresponding to the curves "f," "g," "h," and "i" are manufactured from a square having each side of 2 L, a rectangle having a short side of 2 L and a long side of 3 L, a rectangle having a short side of 2 L and a long side of 4 L, and a rectangle having a short side of 2 L and a long side of 5 L, respectively. Note that the curve "a" in FIG. 10A illustrates the characteristics of one set of Helmholtz coils.

It can be understood from FIGS. 10A to 10C that, when the shape of the coil is modified to a polygonal shape such as a quadrangle or an octagon and the distance between two coils is made different from the distance (the distance between two coils that constitute the Helmholtz coils) of the Helmholtz coils, the magnetic field changes depending on a location and the characteristics of the coils deviate from the characteristics of the Helmholtz coils. On the other hand, it can be understood from FIG. 10A that, when the distance between two coils is the same as the distance of the Helmholtz coils, the closer the size in one direction (the long-side direction) of a coil to the size in the other direction (the short-side direction), and the more the number of corners of the polygonal shape of a coil lager than a quadrangle (that is, the closer the shape to a circle or an ellipse), the more the characteristics of the coils similar to the characteristics of the Helmholtz coil. Moreover, it can be understood from FIGS. 10A to 10C that the more the number of corners of the polygonal shape of a coil lager than a quadrangle (that is, the closer the shape to a circle or an ellipse), the larger the magnetic flux density is obtained. Furthermore, the curves "g," "h," and "i" exhibit smaller dependence on location of the magnetic field than the curve "f" in FIG. 10c. It can be understood that, when the distance between two coils is larger than the distance of the Helmholtz coil, the dependence on location of the magnetic field decreases if the size in one direction (long-side direction) of a polygon is larger than the size in the other direction (short-side direction) so that the size in one direction (long-side direction) of a polygon approaches the distance between the two coils. In the present application, a polygon in which the size in one direction is larger than the size in the other direction orthogonal to the direction is referred to as an oblong polygon.

Figure 12:
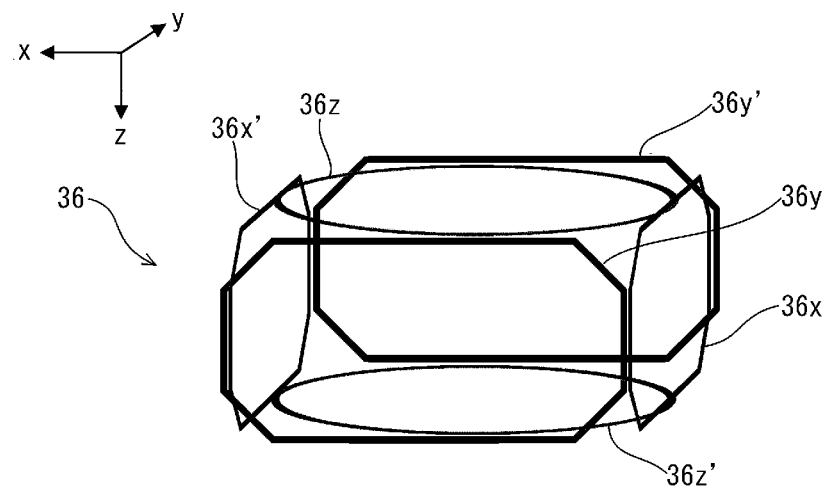
FIG. 12 is a schematic pictorial diagram illustrating a configuration of a modification of the magnetic field generating portion of the medical device.

A magnetic field generating portion 36 includes one set of Helmholtz coils and two sets of coil pairs obtained by modifying the structure (the shape and size of coils and the distance between two coils) of the Helmholtz coils so as to surround the capsule endoscope 2 from three orthogonal directions. As illustrated in FIG. 12, in this example, one set of Helmholtz coils is one set of z-axis Helmholtz coils $36z$ and $36z'$ that generates a magnetic field in the z-axis direction. Moreover, the other two sets of coil pairs are one set of x-axis coil pairs $36x$ and $36x'$ that generates a magnetic field in the x-axis direction and one set of y-axis coil pairs $36y$ and $36y'$ that generates a magnetic field in the y-axis direction.

The magnetic field generating portion 36 enables to decrease an overall size thereof although a change in the magnetic field depending on the location in the x-axis direction and the y-axis direction increases as compared to the magnetic field generating portion 31 having three sets of Helmholtz coils, because it is not necessary in the magnetic field generating portion 36 to arrange a plurality of orthogonal Helmholtz coils so as not to overlap. It is a little difficult to control the magnetic field generating portion 36 because the magnetic field in the x-axis direction and the y-axis direction is not uniform though the magnetic field in the z-axis direction is uniform. However, it is possible to generate the static magnetic field and the alternating magnetic field in a manner similarly to the magnetic field generating portion 31 described above and to control the moving direction and the moving speed of the capsule endoscope 2.

The coils $36x$, $36x'$, $36y$, and $36y'$ that constitute the coil pairs may have a polygonal circumferential shape or an elliptical or circular circumferential shape that is more similar to the shape of the Helmholtz coil. When the distance between the two coils that constitute the coil pair is large, if the coils $36x$, $36x'$, $36y$, and $36y'$ have such an oblong polygonal or elliptical circumferential shape that the size in the y-axis direction or the x-axis direction is larger than the size in the z-axis direction, it is possible to suppress a change in the magnetic field depending on location in the x-axis direction and the y-axis direction while decreasing the size in the z-axis direction.

The present invention is not limited to the magnetic field generating portion 36 but can be modified in various ways. For example, the shape of the coils of any one or two sets of coil pairs or the three sets of coil pairs of the magnetic field generating portion 31 having three sets of Helmholtz coils may be changed and the size of the coils and the distance between two coils may be changed. In this case, the coils that constitute each of the three sets of coil pairs each have a circumferential shape that is selected from a polygonal shape, an elliptical shape, and a circular shape. When the coil has a polygonal circumferential shape, a quadrangular circumferential shape or a polygonal circumferential shape having more corners than a quadrangle which is preferred from the perspective of the above-described characteristics can be used. Moreover, the coils that constitute any one or two sets of the three sets of coil pairs or the three sets of coil pairs may each have a circumferential shape that is an oblong polygonal shape or an elliptical shape which is preferred from the perspective of the above-described characteristics.

Figure 13:
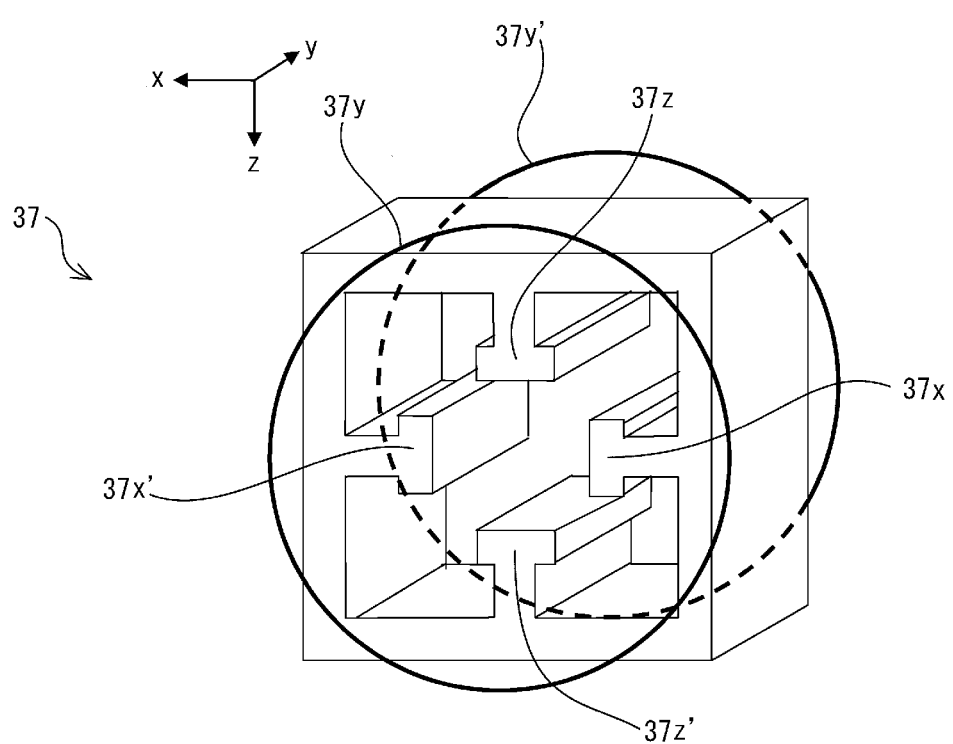
FIG. 13 is a schematic pictorial diagram illustrating a configuration of another modification of the magnetic field generating portion of the medical device.

Moreover, a magnetic field generating portion 37 that includes one set of Helmholtz coils and two sets of electromagnets so as to surround the capsule endoscope 2 from three orthogonal directions may be used. As illustrated in FIG. 13, the magnetic field generating portion 37 includes one set of x-axis electromagnets $37x$ and $37x'$ that generates a magnetic field in the x-axis direction, one set of y-axis Helmholtz coils $37y$ and $37y'$ that generates a magnetic field in the y-axis direction, and one set of z-axis electromagnets $37z$ and $37z'$ that generates a magnetic field in the z-axis direction. The subject may lie or stand up in parallel to the y-axis direction.

Although the magnetic field generating portion 37 including one set of Helmholtz coils and two sets of electromagnets is heavy and generates a magnetic field that is uneven (not uniform), since the size of the electromagnet is small, and the radius and the gap of one set of Helmholtz coils can be freely decreased, it is possible to decrease the overall size. It becomes a little difficult to control the magnetic field generating portion 37 because the magnetic field in the x-axis direction and the z-axis direction is not uniform. However, it is possible to generate the static magnetic field and the alternating magnetic field and to control the moving direction and the moving speed of the capsule endoscope 2.

While the medical device according to the embodiment of the present invention has been described, the present invention can be changed in design in various ways within the scope described in the claims without being limited to those described in the embodiment. For example, the structure and the shape of the endoscope main body 2a of the capsule endoscope 2 may come in various types. Moreover, the shapes of the handle 33a and the joystick 33b of the operating unit 33 of the capsule controller 3 are not limited to particular shapes, and for example, the handle 33a may have a dial shape, a knob shape, or a shape of a joystick that does not stand in addition to the shapes illustrated in FIGS. 6A to 6D. Further, the operating unit 33 of the capsule controller 3 may use a keyboard, a mouse, a touch panel, and the like of a PC instead of the handle 33a, the joystick 33b (and the joystick platform 33b'), and the like so that the same signal as the control signal output from the operating unit 33 according to the operation of the handle 33*a*, the joystick 33*b* (and the joystick platform 33*b'*), and the like is output according to software.

EXPLANATIONS OF REFERENCE NUMERALS

1 Medical device
2 Capsule endoscope
21 Magnet
2*b* Fin portion
3 Capsule controller
31, 36 Magnetic field generating portion
33 Operating unit
33*a* Handle
33*b* Joystick

The invention claimed is:

1. A medical device comprising:
a capsule endoscope in which a fin portion mounting a magnet having a magnetization direction in an axial direction is provided at a rear end in the axial direction of an endoscope main body, and which can be self-propelled through the inside of a body; and
a capsule controller that controls self-propulsion of the capsule endoscope from the outside of the body by generating a static magnetic field whose direction is controlled three-dimensionally and an alternating magnetic field orthogonal to the static magnetic field, wherein
the capsule endoscope is configured such that the capsule endoscope rotates upon receiving the static magnetic field so that the magnetization direction of the magnet is parallel to the direction of the static magnetic field and aligned in a direction identical to a target moving direction and the fin portion vibrates by bending with movement of the magnet in response to the alternating magnetic field being generated simultaneously with and combined with the static magnetic field, whereby propulsive power in the axial direction is generated.

2. The medical device according to claim 1, wherein
the capsule controller generates the static magnetic field and the alternating magnetic field by means of a magnetic field generating portion that includes three sets of Helmholtz coils.

3. The medical device according to claim 1, wherein
the capsule controller generates the static magnetic field and the alternating magnetic field by means of a magnetic field generating portion that includes three sets of coil pairs, and
coils that constitute each of the three sets of coil pairs each have a circumferential shape that is selected from a polygonal shape, an elliptical shape, and a circular shape.

4. The medical device according to claim 3, wherein
coils that constitute any one or two sets of the three sets of coil pairs or the three sets of coil pairs each have a circumferential shape that is an oblong polygonal shape or an elliptical shape.

5. The medical device according to claim 1, wherein
the capsule controller generates the static magnetic field and the alternating magnetic field by means of a magnetic field generating portion that includes one set of Helmholtz coils and two sets of electromagnets.

6. The medical device according to claim 1, wherein
the capsule controller is configured to be able to change an amplitude and/or a frequency of the alternating magnetic field and/or to change a magnitude of the static magnetic field.

7. The medical device according to claim 6, wherein
the amplitude and/or the frequency of the alternating magnetic field and/or the magnitude of the static magnetic field corresponds to a turn angle of a terminal, a tilt angle of a joystick, a moving distance of a lever, or a depression amount of an accelerator.

8. The medical device according to claim 1, wherein
the direction of the static magnetic field is controlled by an operating unit that uses a handle whose rotational position can be held, and corresponds to a direction of a reference point of the handle.

9. The medical device according to claim 8, wherein
an inclination angle of the static magnetic field in relation to a horizontal surface is controlled by changing an inclination angle of a shaft of the handle or by changing a moving distance of a movable portion of a slider or a lever.

10. The medical device according to claim 1, wherein
the direction of the static magnetic field is controlled by an operating unit that uses a joystick, and a reference point of a joystick platform is rotated by an angle corresponding to a tilt direction of the joystick, thus the direction of the static magnetic field corresponds to the direction of the reference point.

11. The medical device according to claim 10, wherein
an inclination angle of the static magnetic field in relation to a horizontal surface is controlled by changing a tilt angle of the joystick platform or by changing a moving distance of a movable portion of a slider or a lever.

\* \* \* \* \*